United States Patent [19]

Upmeyer et al.

[11] Patent Number: 6,028,062
[45] Date of Patent: Feb. 22, 2000

[54] **USE OF DIMETICONE FOR THE LOCAL ANTIBACTERIAL THERAPY AND/OR THE PREVENTION AND THERAPY OF *HELICOBACTER PYLORI* (HP) ASSOCIATED SYNDROMES AND INFECTIOUS DISEASES**

[76] Inventors: Hans-Jürgen Upmeyer, Mauerkircherstrasse 197, 81925 München; Alfred Schmidt, Leinpfad 2, 22301 Hamburg, both of Germany

[21] Appl. No.: 08/716,142
[22] PCT Filed: Mar. 15, 1995
[86] PCT No.: PCT/EP95/00972
§ 371 Date: Jan. 21, 1997
§ 102(e) Date: Jan. 21, 1997
[87] PCT Pub. No.: WO95/25525
PCT Pub. Date: Sep. 28, 1995
[51] Int. Cl.[7] .................................................... A61K 3/695
[52] U.S. Cl. ............................ 514/63; 514/925; 514/928
[58] Field of Search ................................ 514/772, 772.2, 514/772.3, 63, 925–928; 424/78.37, 78.08

[56] References Cited

U.S. PATENT DOCUMENTS

| | | |
|---|---|---|
| 4,837,029 | 6/1989 | Olsen . |
| 5,120,533 | 6/1992 | Schmidt et al. ...................... 424/78.08 |
| 5,229,137 | 7/1993 | Wolfe . |
| 5,277,902 | 1/1994 | Schmidt et al. ..................... 424/78.37 |
| 5,534,544 | 7/1996 | Plaut et al. .............................. 514/473 |

FOREIGN PATENT DOCUMENTS

| | | |
|---|---|---|
| 219076 | 4/1987 | European Pat. Off. . |
| 428296 | 5/1991 | European Pat. Off. . |
| 9007930 | 7/1990 | WIPO . |
| 9104034 | 4/1991 | WIPO . |
| 9403209 | 2/1994 | WIPO . |
| 9505813 | 3/1995 | WIPO . |

OTHER PUBLICATIONS

Gladston, Ted. "American's stress keeps drug store antacid sales burning." Drug Store News, vol. 12, No. 19, p. IP40, Oct. 22, 1990.

Marshall, B.J.: Unidentified Curved Bacilli on Gastric Epithelium in Active Chronic Gastritis; Lancet I (1983), pp. 1273–1275.

Dixon, M.F.: *Helicobacter pylori* and Peptic Ulceration: Histopathological Aspects (1991), pp. 125–130.

*Primary Examiner*—Mary E. Mosher
*Attorney, Agent, or Firm*—Birch, Stewart, Kolasch & Birch, LLP

[57] ABSTRACT

The invention relates to the use of dimethylpolysiloxane (dimeticone) for the local antibacterial therapy and the prevention and treatment of syndromes and infections associated with *Helicobacter pylori*.

2 Claims, No Drawings

USE OF DIMETICONE FOR THE LOCAL ANTIBACTERIAL THERAPY AND/OR THE PREVENTION AND THERAPY OF *HELICOBACTER PYLORI* (HP) ASSOCIATED SYNDROMES AND INFECTIOUS DISEASES

This is a 371 of International Application PCT/EP95/00972, filed Mar. 15, 1995.

TECHNICAL FIELD OF THE INVENTION

The invention relates to the use of dimethylpolysiloxane (dimeticone) for the local antibacterial therapy and the prevention and treatment of syndromes and infections associated with *Helicobacter pylori* (*Hp*).

BACKGROUND OF THE INVENTION

Commercial dimeticone-containing products such as for instance sab simplex® and Lefax® (see the Rote Liste 1993) are used to treat flatulence and to prepare patients for sonography.

WO 90/07930 discloses the use of dimethylpolysiloxane, in particular in conjunction with silica gel in the treatment of diseases of the esophagus, the stomach and the duodenum, such as esophagitis, ulcera (ventriculi and duodeni) and gastrites. Said document describes the capability of dimeticone to form and maintain a protective film in the esophagus, the stomach and the duodenum after oral administration.

In recent years, it has become known that in some forms of chronic gastritis and in the development of ulcera (ulcus ventriculi and duodeni), the infection of the gastro-intestinal (GI) tract with the gram negative pathogen *Hp* is a pathogenetic factor, and its relationship to the genesis of gastric carcinoma is being increasingly discussed.

Although it has been known among pathologists since the close of the 19th century that spiral bacteria are present in the stomach mucosa, it was not until 1983 that *Hp* was cultured from bioptic material of the antrum mucosa of patients afflicted with peptic ulcera and gastritis. (Marshall, B. J.: Unidentified curved bacilli on gastric epithelium in active chronic gastritis. Lancet I (1983), 1273–1275).

*Hp* is acid-instable and sensitive to competition from other bacteria. Hence, the pathogen can only grow in a particular ecological niche. It finds this niche directly underneath the protective mucosa layer on the epithelium of the antrum and the body mucosa, but also on gastric metaplasies of the duodenal mucosa.

The route of *Hp* infection has not, so far, been elucidated. The infection was thought likely to be passed on orally from man to man, especially since it has not yet been possible to establish a pathogen reservoir of animal origin. The rate of infection depends on sanitation standards. In Western industrialized countries, the infection rate is about 1% per year. Hence, *Hp* infections are found in 60% of the persons aged 60.

The association of the *Hp* pathogen with different symptoms of the upper GI tract was systematically investigated in the past few years. The high prevalence of *Hp* infection in a population not afflicted with ulcus initially led to the assumption that *Hp* is a harmless saprophyte. Nowadays it is considered an established fact that the pathogen causes the B-type gastritis in the mucosa of the stomach. (Dixon, M. F.: *Helicobacter pylori* and peptic ulceration: Histopathological aspects. J. Gastroenterol. Hepatol. 6 (1991), 125–130).

The B-type gastritis is closely related to *Hp* infection which is detected in almost 100% of these patients.

The B-type gastritis is almost always present in patients suffering from ulcus duodeni, although the pathogenetic relationship is still unclear.

Experiences made in many years with acid blockers not possessing an antibacterial effect against *Hp*, have shown that ulcera can be cured even in cases of persistent *Hp* growth. About 10% of the patients cured from *Hp* by an antibacterial therapy, show an ulcus relapse within a year. Admittedly, these patients, as a rule, also suffer from an *Hp* re-infection. It must remain an open question why the relapse of the *Hp* infection in these patients is sufficient to cause an ulcus relapse within a year, when 40% of the population not afflicted with ulcera are *Hp* positive.

Ulcus ventriculi is also considered to be associated with *Hp*. In this case, the correlation with the *Hp* infection is not as close, as only 70–80% of the patients with gastric ulcera are *Hp* positive (Marshall, B. J., loc. cit.).

SUMMARY OF THE INVENTION

Surprisingly, dimeticone has been found to be effective in the local antibacterial therapy of *Hp* infections and the prevention and treatment of *Hp* associated diseases, as it reduces *Hp* growth.

Therefore, the invention relates to the use of dimeticone for the local antibacterial therapy and the prevention and treatment of *Hp* associated diseases, in particular the prevention and treatment of gastritis, ulcus ventriculi, ulcus duodeni and gastric carcinoma.

In a randomized clinical comparative test, dimeticone was found to significantly reduce the growth of *Hp* in test persons with diagnosed ulcus ventriculi, when it was administered in a dose of 80 mg four times a day over 4 weeks. A similar result was not achieved with ranitidine administered in a dose of 300 mg for 4 weeks in the evening.

In a gastroscopic investigation of the stomach, the *Hp* growth was examined by an additional biopsy of the antrum mucosa. The results of this study are summarized in the following table.

TABLE

| Helicobacter pylori | Dimeticone $T_o$ | (N = 27) $T_1$ | Ranitidine $T_o$ | (N = 30) $T_1$ |
|---|---|---|---|---|
| not present | 2/9.5% | 11/52.4% | 2/13.6% | 4/18.2% |
| little | 9/42.9% | 5/23.8% | 9/40.9% | 13/59.1% |
| medium | 8/38.1% | 5/23.8% | 6/27.3% | 4/18.2% |
| much | 2/9.5% | 0/0.0% | 4/18.2% | 1/4.5% |

$T_o$ = without treatment
$T_1$ = after a 4-week treatment

The foregoing data clearly show that the administration of dimeticone leads to a significant reduction of the *Hp* growth. In 52.4% of the patients treated with dimeticone, the pathogen could no longer be detected after a 4 week treatment.

According to the invention, dimeticone may be used either alone or in combination with other active ingredients, such as antibiotics, e.g. amoxicillin, tetracycline, clathromycin or metronidazole and/or proton-pump-inhibitors, $H_2$-blockers, antacids or antitumor agents.

While we have described an embodiment of this invention, it is apparent that our embodiment may be altered to provide other embodiments which utilize the method of this invention. Therefore, it will be appreciated that the scope of this invention is to be defined by the appended claims, rather than by the specific embodiment which has been presented by way of example.

We claim:

1. A method for the local antibacterial treatment of *Helicobacter pylori* infection which comprises administering an effective amount of dimethicone to a patient in need thereof for 4 weeks.

2. A method for the local antibacterial treatment of *Helicobacter pylori* infection which comprises administering a dose of 80 mg of dimethicone to a patient in need thereof, four times a day over 4 weeks.

* * * * *